United States Patent
Onuma et al.

(10) Patent No.: US 10,492,818 B2
(45) Date of Patent: Dec. 3, 2019

(54) TREATMENT METHOD

(71) Applicant: OLYMPUS CORPORATION, Hachioji-shi, Tokyo (JP)

(72) Inventors: Chie Onuma, Tama (JP); Yasuo Tanigami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 296 days.

(21) Appl. No.: 15/291,805

(22) Filed: Oct. 12, 2016

(65) Prior Publication Data
US 2018/0098784 A1 Apr. 12, 2018

(51) Int. Cl.
*A61B 17/32* (2006.01)
*A61B 17/00* (2006.01)
*A61B 90/00* (2016.01)

(52) U.S. Cl.
CPC .......... *A61B 17/320068* (2013.01); *A61B 2017/0003* (2013.01); *A61B 2017/00977* (2013.01); *A61B 2090/065* (2016.02); *A61B 2090/0807* (2016.02)

(58) Field of Classification Search
CPC .... A61B 17/320068; A61B 17/320016; A61B 2017/0003; A61B 2017/00185; A61B 2017/00977; A61B 2090/065
See application file for complete search history.

(56) References Cited

U.S. PATENT DOCUMENTS

| | | | |
|---|---|---|---|
| 2007/0149881 A1* | 6/2007 | Rabin | A61B 17/32002 600/471 |
| 2009/0143806 A1* | 6/2009 | Witt | A61B 17/320092 606/169 |
| 2017/0000554 A1* | 1/2017 | Yates | A61B 18/1445 |

FOREIGN PATENT DOCUMENTS

JP 2003-235862 A 8/2003

* cited by examiner

*Primary Examiner* — Ashley L Fishback
(74) *Attorney, Agent, or Firm* — Oliff PLC

(57) ABSTRACT

A treatment method is a treatment method for cutting cartilage of a human body by an ultrasonic device including a cutting section that ultrasonically vibrates. The treatment method includes cutting the cartilage with a product of an amplitude of the cutting section and a pressing force for pressing the cutting section against the cartilage being 100 (N·μm) or larger.

6 Claims, 8 Drawing Sheets

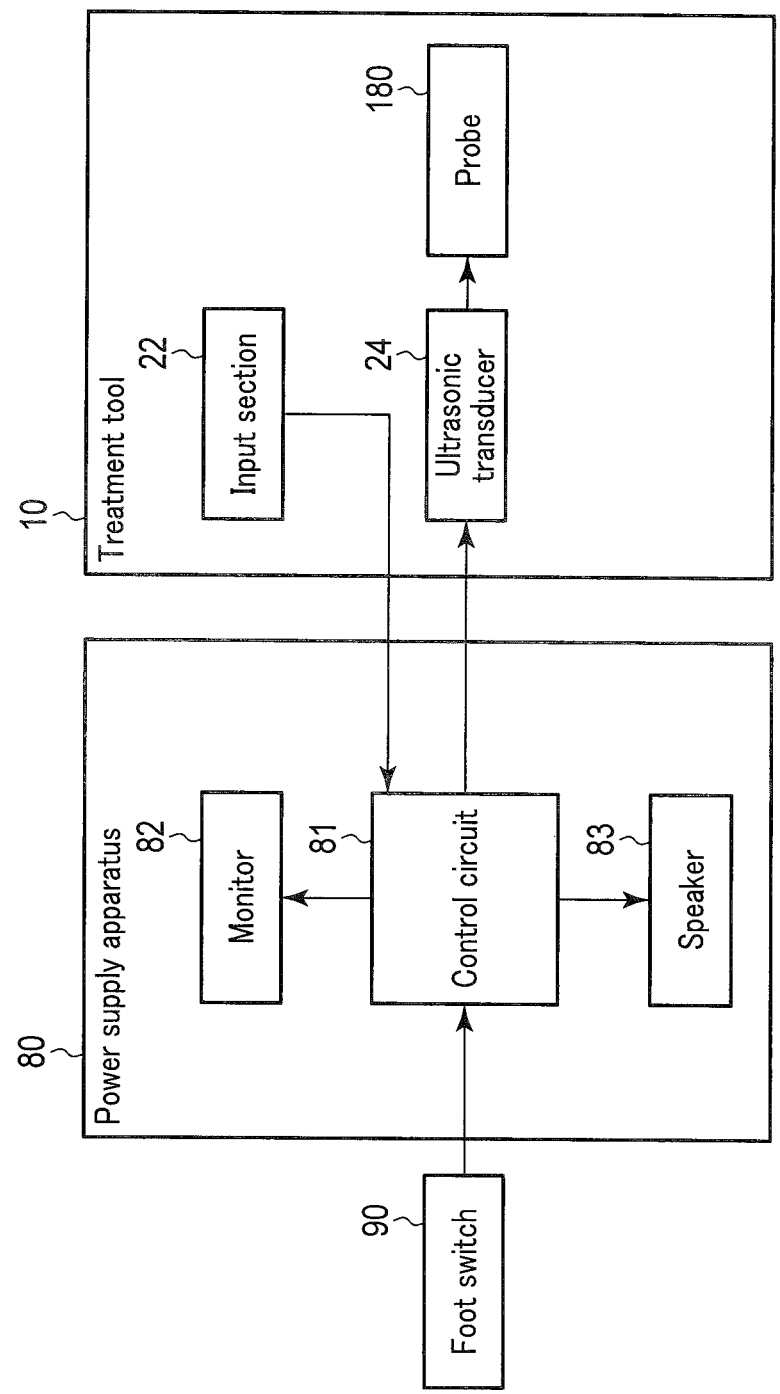
F I G. 2

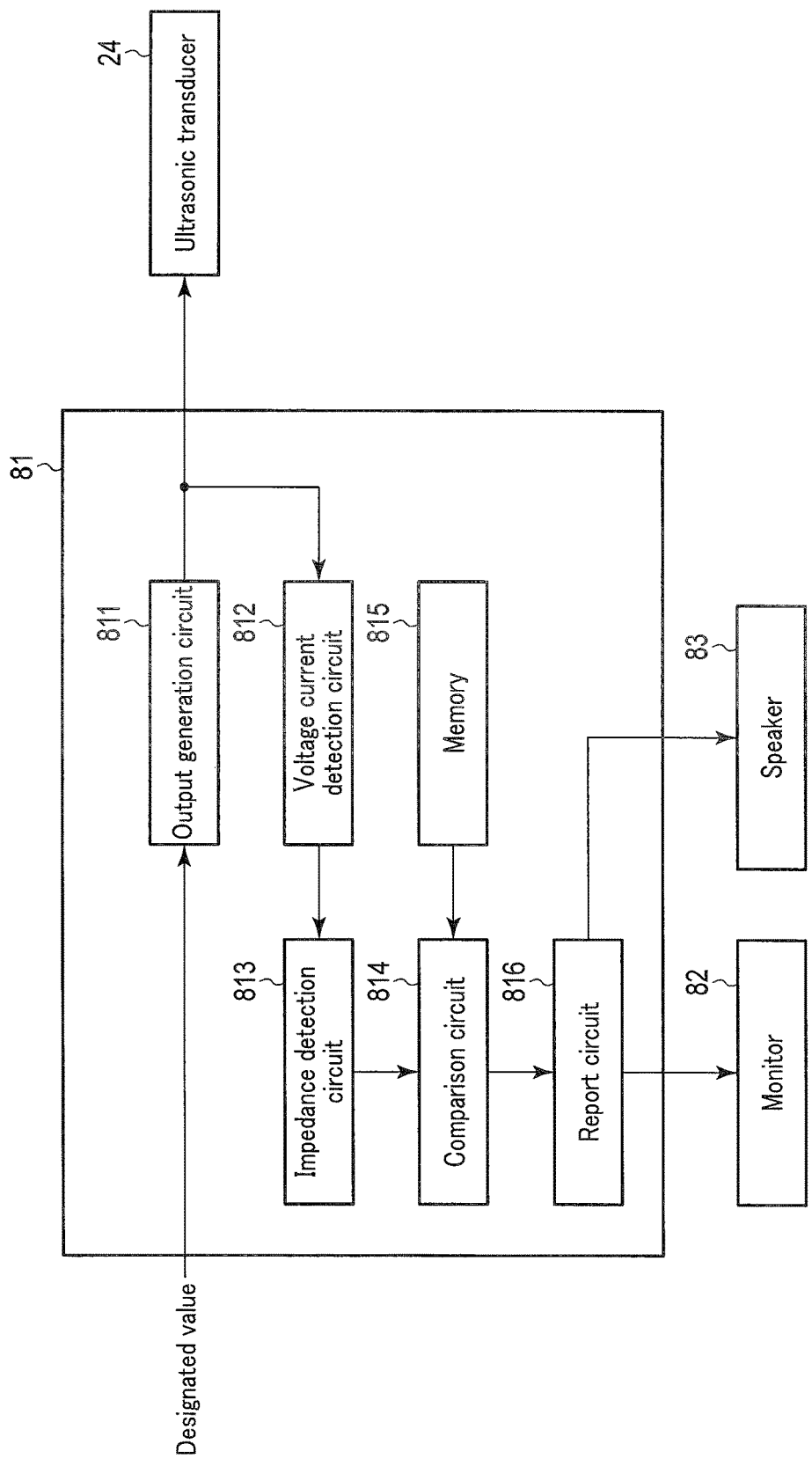
F I G. 3

Cut amount change when pressing force and output (amplitude) is changed (cartilage) N=6

Relationship between "(pressing force)*(amplitude)" and cut amount (cartilage)

TREATMENT METHOD

BACKGROUND OF THE INVENTION

1. Field of the Invention

The present invention relates to a treatment method.

2. Description of the Related Art

An ultrasonic surgical instrument is known as one of the treatment tools for treating body tissue. The ultrasonic surgical instrument is configured to press a probe that is ultrasonically vibrating against body tissue, which is a subject, so as to treat the body tissue. For efficient treatment, it is important to perform pressing with an appropriate pressing force. Therefore, for example, the ultrasonic surgical instrument proposed in Jpn. Pat. Appln. KOKAI Publication No. 2003-235862 is configured to use a spring which mechanically changes in accordance with a pressing force of a probe brought into contact with body tissue and detection means for detecting the change of the spring so as to detect the pressing force, and to generate ultrasonic vibration when the detected pressing force falls within a desired range.

BRIEF SUMMARY OF THE INVENTION

A treatment method of one aspect of the present invention is a treatment method for cutting cartilage of a human body by an ultrasonic device including a cutting section that ultrasonically vibrates, the treatment method comprising: cutting the cartilage with a product of an amplitude of the cutting section and a pressing force for pressing the cutting section against the cartilage being 100 (N·µm) or larger.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram showing a main configuration of an ultrasonic device in a first embodiment;

FIG. 3 is a block diagram showing a configuration of a control circuit in the first embodiment;

DETAILED DESCRIPTION OF THE INVENTION

Hereinafter, embodiments of the present invention will be described with reference to the drawings.

First Embodiment

Figure 1:
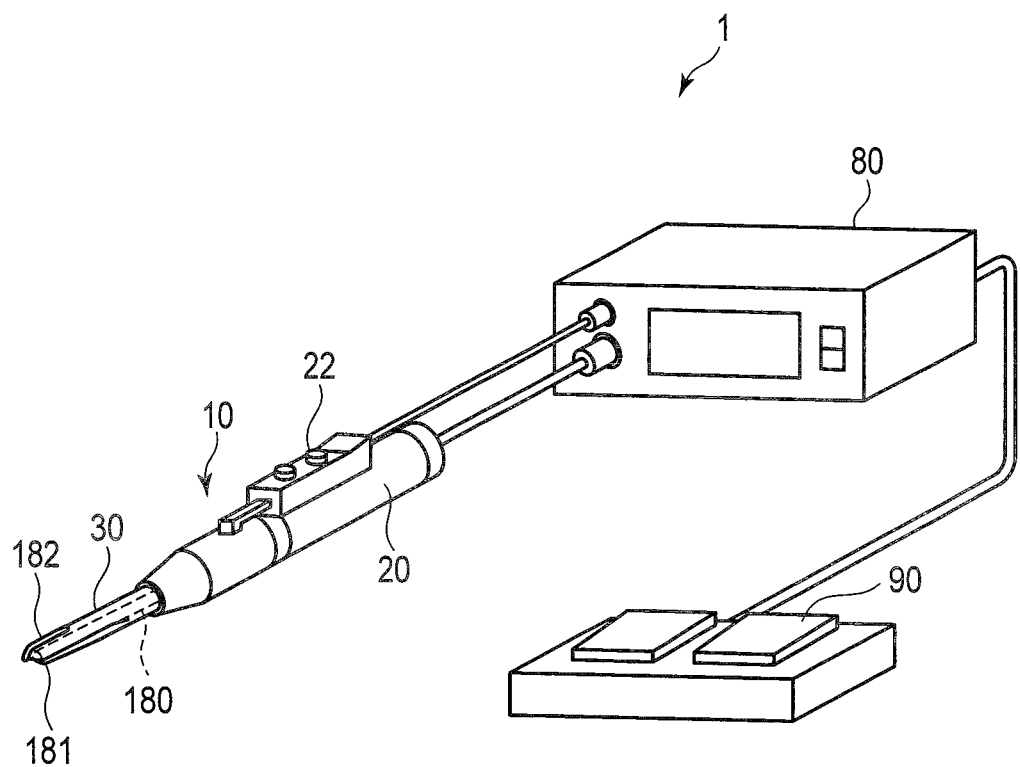
FIG. 1 shows a configuration of an ultrasonic device as one example of an ultrasonic surgical instrument according to each embodiment.

The first embodiment of the present invention will be described. FIG. 1 shows a configuration of an ultrasonic device 1 as one example of an ultrasonic surgical instrument according to each embodiment of the present invention. The ultrasonic device 1 includes: a treatment tool 10 for treating body tissue by ultrasonic waves; a power supply apparatus 80 that supplies the treatment tool 10 with drive power; and a foot switch 90. The ultrasonic device 1 has a cortical bone/cancellous bone cutting mode, which is a mode suitable for cutting hard bone such as cortical bone, and a cartilage cutting mode, which is a mode suitable for cutting cartilage. However, the ultrasonic device 1 may also be used for a treatment other than cutting of bone.

The treatment tool 10 includes: a hand piece 20; a probe 180 protruding from the hand piece 20; and a thin and long sheath 30 formed around the probe 180. In the following descriptions, the probe 180 side in the treatment tool 10 is called a "distal end side" of the treatment tool 10, and the hand piece 20 side is called a "proximal end side."

The hand piece 20 includes therein an ultrasonic transducer. The ultrasonic transducer ultrasonically vibrates in accordance with the drive power from the power supply apparatus 80. The hand piece 20 conveys ultrasonic vibration generated at the ultrasonic transducer to the probe 180. The probe 180 is connected to the ultrasonic transducer and vibrates in accordance with the vibration of the ultrasonic transducer.

The distal end of the sheath 30 is shaped like a half round cylinder, and a cutting section 181 provided at the distal end of the probe 180 is exposed from the portion shaped like a half round cylinder. In addition, for example, a cold knife 182 is formed at the distal end of the sheath 30. The cold knife 182 is made of a corrosive-resistant metallic material, and is used to facilitate cutting of body tissue. The cold knife 182 is not necessarily provided.

The hand piece 20 includes an input section 22. The input section 22 is a section for inputting instructions to drive the ultrasonic transducer. The input section 22 may include a plurality of switches for switching between the cortical bone/cancellous bone cutting mode and the cartilage cutting mode. The input section 22 is connected to the power supply apparatus 80. The ultrasonic transducer in the hand piece 20 is connected to the power supply apparatus 80. The power supply apparatus 80 detects an input to the input section 22, and supplies the ultrasonic transducer with drive power corresponding to the input.

The foot switch 90 has the same function as that of the input section 22 provided in the hand piece 20. Namely, like the input section 22, the foot switch 90 may include a plurality of switches for switching between the cortical bone/cancellous bone cutting mode and the cartilage cutting mode. Upon detection of an input to the foot switch 90, the power supply apparatus 80 supplies the ultrasonic transducer with drive power corresponding to the input. At least one of the input section 22 and the foot switch 90 needs to be provided.

When performing treatment, a user holds the hand piece 20, and brings the cutting section 181 provided in the probe 180 that ultrasonically vibrates into contact with body tissue to be treated. At this time, the user operates the input section 22 or the foot switch 90 to vibrate the ultrasonic transducer. The vibration generated at the ultrasonic transducer is conveyed to the probe 180. By bringing the cutting section 181 of the vibrating probe 180 into contact with body tissue, the body tissue is subjected to treatment, such as cutting.

FIG. 2 is a block diagram showing a main configuration of the ultrasonic device 1 in the first embodiment of the present invention. In FIG. 2, the same elements as those in FIG. 1 will be assigned the same reference numerals as those in FIG. 1 to omit their descriptions.

As shown in FIG. 2, the power supply apparatus 80 includes: a control circuit 81; a monitor 82; and a speaker 83.

The control circuit 81 is configured as an IC including, for example, an output generation circuit that generates drive power of the ultrasonic transducer 24, and a circuit that reports to an operator whether the operator's pressing of the probe 180 is appropriate. The control circuit 81 controls the drive power of the ultrasonic transducer 24 in accordance with the input from the input section 22 or the foot switch 90. The control circuit 81 detects an operator's pressing force of the probe 180 against body tissue, which is a subject, and reports to the operator whether the current pressing of the probe 180 is appropriate in accordance with the detected pressing force, by using, for example, a monitor 82, a speaker 83, or both.

The monitor 82 is, for example, a liquid crystal display and displays various types of images based on control by the control circuit 81. The speaker 83 emits various types of voices based on control by the control circuit 81.

FIG. 3 is a block diagram showing a configuration of the control circuit 81 in the first embodiment. The control circuit 81 includes an output generation circuit 811, a voltage current detection circuit 812, an impedance detection circuit 813, a comparison circuit 814, a memory 815, and a report circuit 816.

The output generation circuit 811 includes a power generation circuit, such as a regulator. In response to an operation of the input section 22 or the foot switch 90, the output generation circuit 811 generates drive power of the ultrasonic transducer 24 so that the ultrasonic transducer 24 vibrates with an amplitude corresponding to the designated value from the input section 22 or the foot switch 90.

The amplitude in the cartilage cutting mode is set higher than that in the cortical bone/cancellous bone cutting mode. This is because cutting is performed mainly by friction heat generated by ultrasonic vibration in the cartilage cutting mode. The quantity of heat Q[J] generated when an object having a mass m[kg] slides on a rough horizontal surface having a kinetic friction coefficient $\mu°$ by s[m] is expressed by the following equation (Equation 1), where the acceleration of gravity is g(m/s$^2$):

$$Q = \mu'mgs \quad \text{(Equation 1)}$$

In Eq. 1, when the pressing force is the normal component of the force relative to the rough surface, the magnitude of the pressing force (N) of the probe 180 is considered to correspond to "mg" in the equation. In addition, "s" corresponds to the amplitude of vertical vibration of the ultrasonic probe. Therefore, if the pressing force is constant, the cut amount of cartilage increases as the amplitude of the probe 180 increases. Thus, in the cartilage cutting mode, the amplitude of ultrasonic vibration is set to be as large as possible to improve cutting efficiency. In the cortical bone/cancellous bone cutting mode, cutting is performed by an impact caused by ultrasonic vibration, rather than friction heat caused by ultrasonic vibration. In the cortical bone/cancellous bone cutting mode, friction heat caused by ultrasonic vibration does not contribute much to cutting. Here, the pressing force is the normal component of the force relative to the rough surface; however, the pressing force may be regarded as, for example, a force of the state having an angle relative to the normal.

The voltage current detection circuit 812 detects each of the output voltage and output current of the output generation circuit 811.

The impedance detection circuit 813 calculates an impedance of the ultrasonic transducer 24 from the ratio between the output voltage and output current detected at the voltage current detection circuit 812. The impedance of the ultrasonic transducer 24 may change depending on the pressing force of the probe 180 against body tissue. Therefore, the impedance detection circuit 813 functions as a detection circuit (sensor) that indirectly detects a pressing force of the probe 180 by detecting the impedance of the ultrasonic transducer 24. The impedance of the ultrasonic transducer 24 may change depending on the type or temperature of body tissue against which the ultrasonic transducer 24 is pressed. Thus, when a pressing force is calculated based on an impedance, it is desirable to correct the value of the impedance in accordance with the type or temperature of body tissue. In addition, the influence of the change in the pressing force on the impedance is smaller than the influence of the change in the type or temperature of body tissue. Therefore, when a pressing force is calculated based on an impedance, the influence of the type or temperature of body tissue may be ignored.

The comparison circuit 814 converts the value of the impedance detected at the impedance detection circuit 813 into a value of a pressing force. The comparison circuit 814 then compares the value of the pressing force obtained by conversion with a pressing force range stored in the memory 815. The comparison circuit 814 then instructs the report circuit 816 to make a report corresponding to the comparison result of the pressing force.

The memory 815 stores the pressing force range. If the pressing force decreases, the cut amount decreases, which results in a longer surgery time. If the pressing force increases, the cut amount increases, but heat intrusion to surrounding tissue also increases. Accordingly, the pressing force range is determined in accordance with the balance between the cut amount and heat intrusion. Different pressing force ranges are used for the cortical bone/cancellous bone cutting mode and the cartilage cutting mode. The details will be described later. The memory 815 stores a table for converting the value of the impedance detected at the impedance detection circuit 813 into a value of a pressing force. This table is obtained by, for example, actually measuring the change in the impedance made when variously changing the pressing force of the probe 180 while keeping the amplitude of the probe 180 at a constant value.

The report circuit 816 makes a report to an operator by using the monitor 82 and the speaker 83 in accordance with instructions from the comparison circuit 814. The report tells whether an operator's pressing of the probe 180 is appropriate, strong, or weak. The report may instruct a user to weaken pressing when the pressing is strong, and to strengthen pressing when the pressing is weak. The report may be made by displaying, for example, a gage indicating a pressing force.

Figure 4:
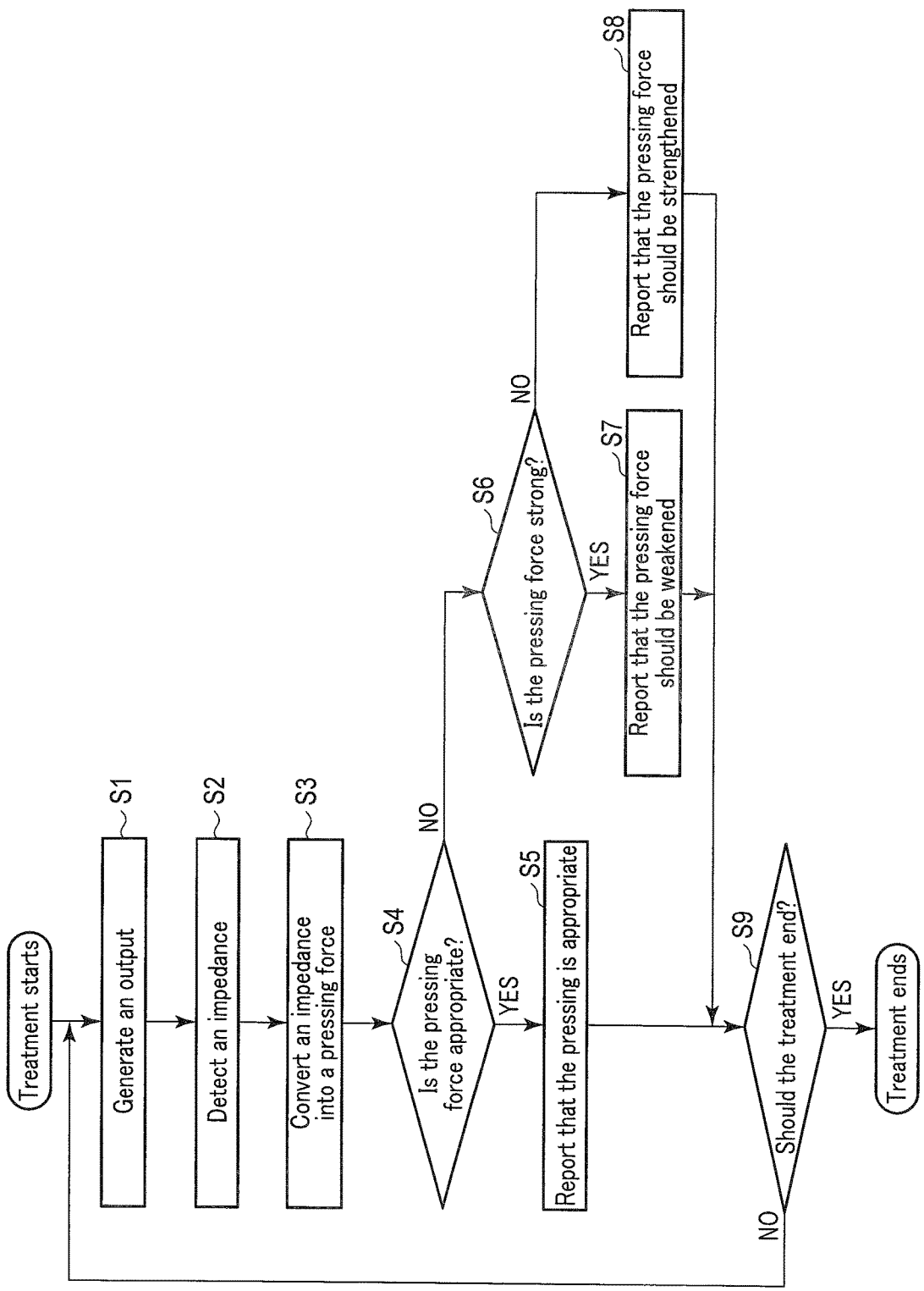
FIG. 4 is a flowchart showing an operation of the ultrasonic device.

Hereinafter, an operation of the ultrasonic device 1 according to the present embodiment will be described. FIG. 4 is a flowchart showing an operation of the ultrasonic device 1. The processing shown in FIG. 4 is started when, for example, the ultrasonic device 1 is turned on, and the input section 22 or the foot switch 90 is operated.

In step S1, the output generation circuit 811 generates drive power for driving the ultrasonic transducer 24. When the input section 22 or the foot switch 90 designates the cartilage cutting mode, the output generation circuit 811 generates drive power to generate ultrasonic vibration with an amplitude corresponding to a designated value set in advance for the cartilage cutting mode. In contrast, when the input section 22 or the foot switch 90 designates the cortical bone/cancellous bone cutting mode, the output generation circuit 811 generates drive power to generate ultrasonic vibration with an amplitude corresponding to a designated value set in advance for the cortical bone/cancellous bone cutting mode. The output generation circuit 811 may be configured to perform feedback control on drive power. In this case, for example, the output current of the output generation circuit 811 detected at the voltage current detection circuit 812 is returned to the output generation circuit 811. The output generation circuit 811 controls the output voltage so that the returned output current matches the designated value.

In step S2, the impedance detection circuit 813 calculates an impedance of the ultrasonic transducer 24 from the ratio between the output voltage and output current detected by the voltage current detection circuit 812.

In step S3, the comparison circuit 814 converts the value of the impedance calculated at the impedance detection circuit 813 into a value of a pressing force in accordance with the table stored in advance in the memory 815.

In step S4, the comparison circuit 814 compares the value of the current pressing force obtained from the value of the impedance with the pressing force range stored in advance in the memory 815. Based on the comparison result, the comparison circuit 814 determines whether the operator's pressing force of the probe 180 is appropriate. For example, if the value of the current pressing force falls within the pressing force range stored in advance in the memory 815, the pressing force is determined as appropriate.

Figure 5:
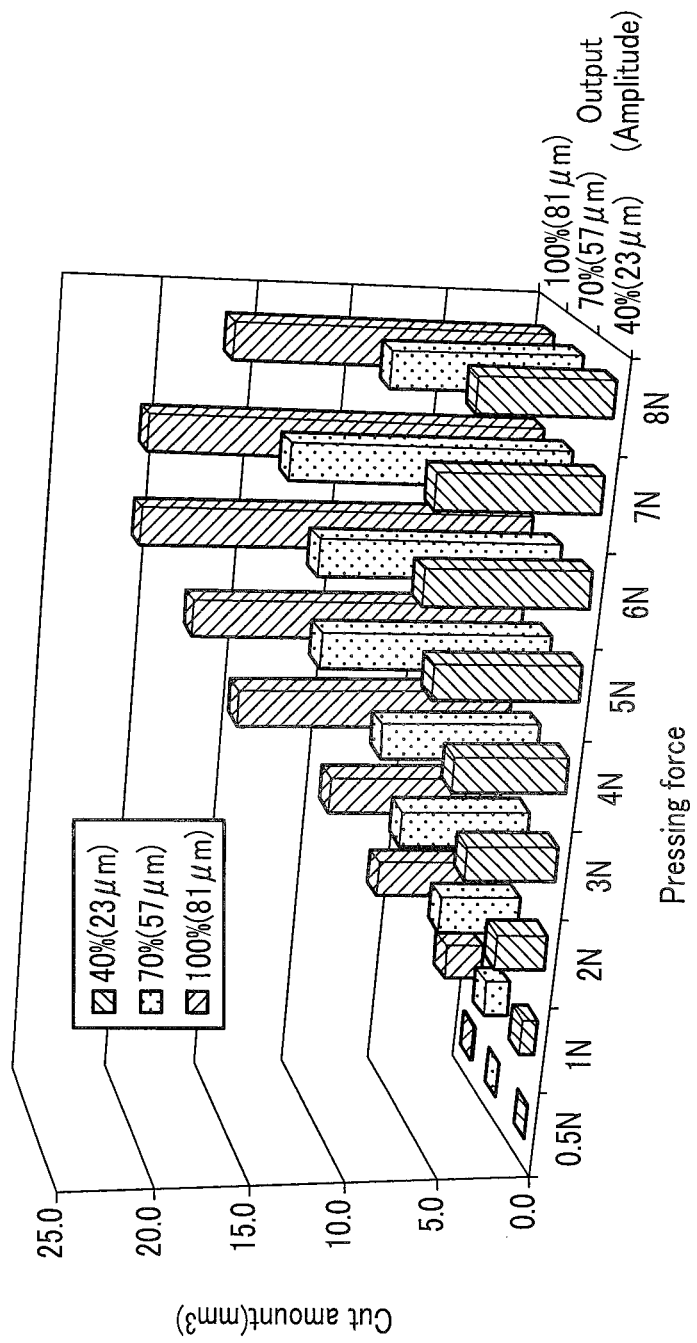
FIG. 5 is a graph showing a result of an experiment for measuring a change in the cut amount in the case where the amplitude or the pressing force against cortical bone is changed.

The pressing force range will be described below. FIG. 5 is a graph showing a result of an experiment for measuring a change in the cut amount in the case where the amplitude or pressing force against cortical bone is changed. In the experiment, the cut amount (volume of the cut cortical bone) is measured when a vibration jig having a variable amplitude and pressing force is pressed against six points (N=6) of the cortical bone to be measured. In the graph of FIG. 5, an average value of the cut amounts at the six points is shown as the cut amount. The value of the amplitude is expressed by a percentage relative to the maximum amplitude (81 μm) of the jig used in the experiment.

As shown in FIG. 5, in the case of cortical bone, the overall trend is that a larger amplitude results in a larger cut amount under the same pressing force, and a larger pressing force results in a larger cut amount under the same amplitude. However, when the pressing force is 0.5(N) or lower, the cut amount does not increase even if the amplitude increases. The cut amount does not increase, either, when pressing force is larger than 8(N). As described above, cortical bone is cut mainly by an impact caused by ultrasonic vibration. Therefore, if the efficiency in conveying the impact caused by ultrasonic vibration decreases due to a pressing force that is too weak or too strong, the cut amount inevitably decreases. According to the graph of FIG. 5, the pressing force range in the cortical bone/cancellous bone cutting mode is 3(N)-5(N) when the amplitude is 40% (23 μm), 2(N)-6(N) when the amplitude is 70% (57 μm), and 1(N)-7(N) when the amplitude is 100% (81 μm). Those values are stored in the memory 815.

Figure 6A:
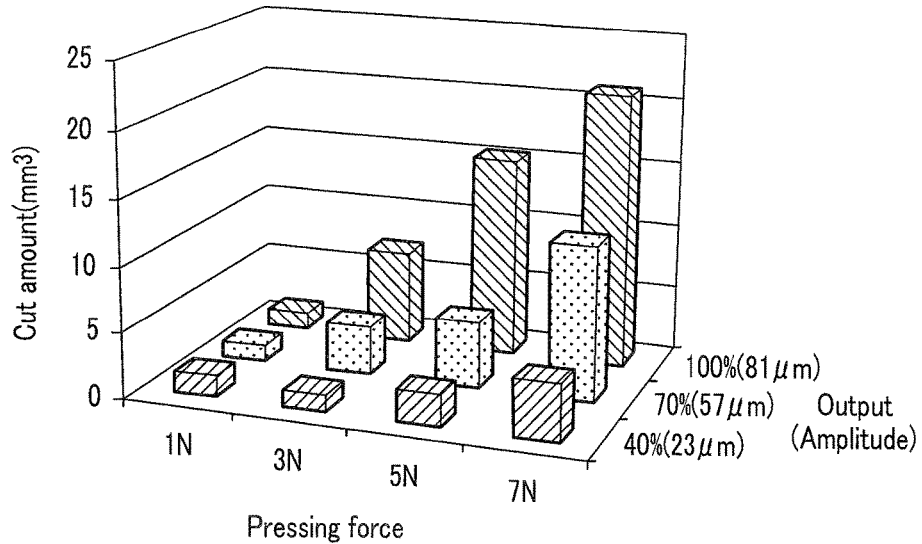
FIG. 6A is a graph showing a result of an experiment for measuring changes in the cut amount in the case where the amplitude or pressing force against cartilage is changed.

FIG. 6A is a graph showing a result of an experiment for measuring a change in the cut amount in the case where the amplitude or pressing force against cartilage is changed. FIG. 6A also shows an average value of the cut amounts (volume of the cut cortical bone) at six points (N=6) of cartilage to be measured. The value of the amplitude is expressed by a percentage relative to the maximum amplitude (81 μm) of the jig used in the experiment.

Figure 6B:
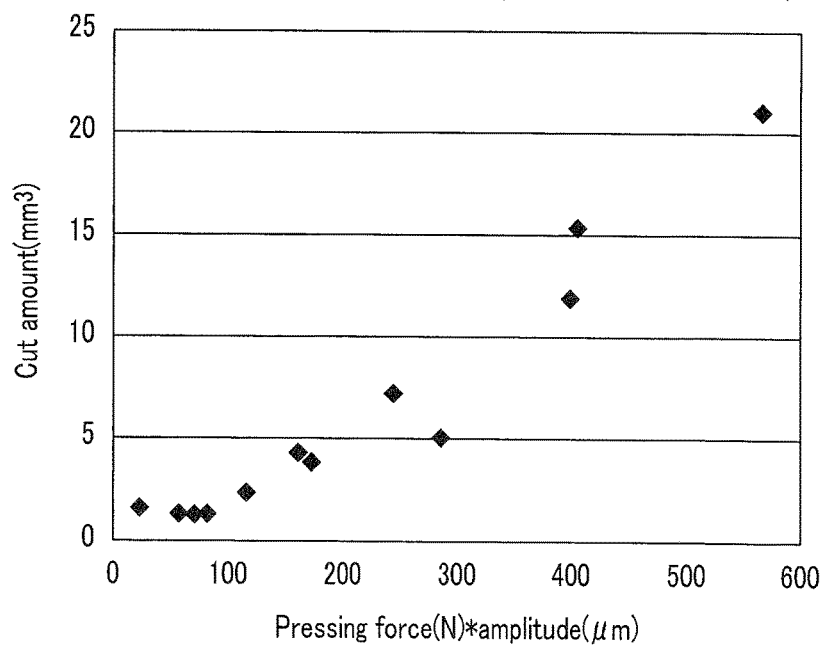
FIG. 6B is a graph in which the lateral axis indicates (pressing force)*(amplitude) and the vertical axis Indicates the cut amount based on the result of FIG. 6A.

As shown in FIG. 6A, in the case of cartilage, the overall trend is that a larger amplitude results in a larger cut amount under the same pressing force, and a larger pressing force results in a larger cut amount under the same amplitude. Unlike cortical bone, cartilage does not dissolve and cutting does not advance under 100 [N·μm] or lower. This is because cartilage is cut mainly by friction heat caused by ultrasonic vibration. FIG. 6B is a graph in which the lateral axis indicates (pressing force)*(amplitude) and the vertical axis indicates the cut amount based on the result of FIG. 6A. When the value of (pressing force)*(amplitude) (corresponding to the quantity of heat) is too large, heat intrusion increases although the cut amount also increases. Therefore, for example, the pressing force range in the cartilage cutting mode are values which allow the value of (pressing force) *(amplitude) to fall within the range of 100 [N·μm]-300 [N·μm]. Those values are stored in the memory 815.

In this way, the comparison circuit 184 compares the pressing force range fixed by the relationship shown in FIG. 5 or 6B with the current pressing force. If the pressing force is determined as appropriate in step S4, the processing moves to step S5. If the pressing force is determined as inappropriate in step S4, the processing moves to step S6.

In step S5, the comparison circuit 814 notifies the report circuit 816 that the pressing force is appropriate. Upon receipt of the notice, the report circuit 816 reports to an operator that the operator's current pressing force is appropriate by using the monitor 82 and the speaker 83. Then, the processing moves to step S9. The report is made by displaying a message, such as "pressing is appropriate", on the monitor 82, or emitting a voice from the speaker 83, or both.

In step S6, the comparison circuit 814 determines whether operator's pressing force of the probe 180 is strong. For example, if the value of the current pressing force exceeds the pressing force range stored in advance in the memory 815, the pressing force is determined as strong. In contrast, if the value of the current pressing force is below the pressing force range stored in advance in the memory 815, the pressing force is determined as weak. If the pressing force is determined as strong in step S6, the processing moves to step S7. If the pressing force is determined as weak in step S6, the processing moves to step S8.

In step S7, the comparison circuit 814 notifies the report circuit 816 that the pressing force is strong. Upon receipt of the notice, the report circuit 816 reports to an operator that the operator's pressing should be weakened by using the monitor 82 and the speaker 83. Then, the processing moves to step S9. The report is made by displaying a message such as "press more weakly" on the monitor 82, or emitting a voice from the speaker 83, or both.

In step S8, the comparison circuit 814 notifies the report circuit 816 that the pressing force is weak. Upon receipt of the notice, the report circuit 816 reports to an operator that the operator's pressing should be strengthened by using the monitor 82 and the speaker 83. Then, the processing moves to step S9. The report is made by displaying a message such as "press more strongly" on the monitor 82, or emitting a voice from the speaker 83, or both.

In step S9, the output generation circuit 811 determines whether to finish the processing. For example, the processing is determined to be finished when the ultrasonic device 1 is turned off, or when the operation of the input section 22 or the foot switch 90 is canceled. When the processing is determined to be finished in step S9, the processing in FIG. 4 ends. If the pressing force is determined not to be finished in Step S9, the processing returns to step S1.

As described above, according to the present embodiment, an operator's pressing force of the probe 180 against body tissue is compared with a predetermined pressing force range, and whether or not the operator's pressing is appropriate is reported based on the comparison result. The operator can thereby perform treatment with an appropriate pressing force.

In addition, different pressing force ranges are used for the cortical bone/cancellous bone cutting mode and the cartilage cutting mode in the present embodiment. This allows the operator to perform pressing based on only the report from the ultrasonic device 1 without regard to the difference between the cortical bone/cancellous bone cutting mode and the cartilage cutting mode.

The steps in the processing of FIG. 4 are performed by using a "circuit," but may be performed by software.

Second Embodiment

Hereinafter, the second embodiment of the present invention will be described. In the first embodiment, the current pressing force is compared with a range, and a report is made for the operator in accordance with the comparison result. In the second embodiment, the current pressing force is compared with a pressing force range, and feedback control is performed on the amplitude of an ultrasonic transducer 24 in accordance with the comparison result.

Figure 7:
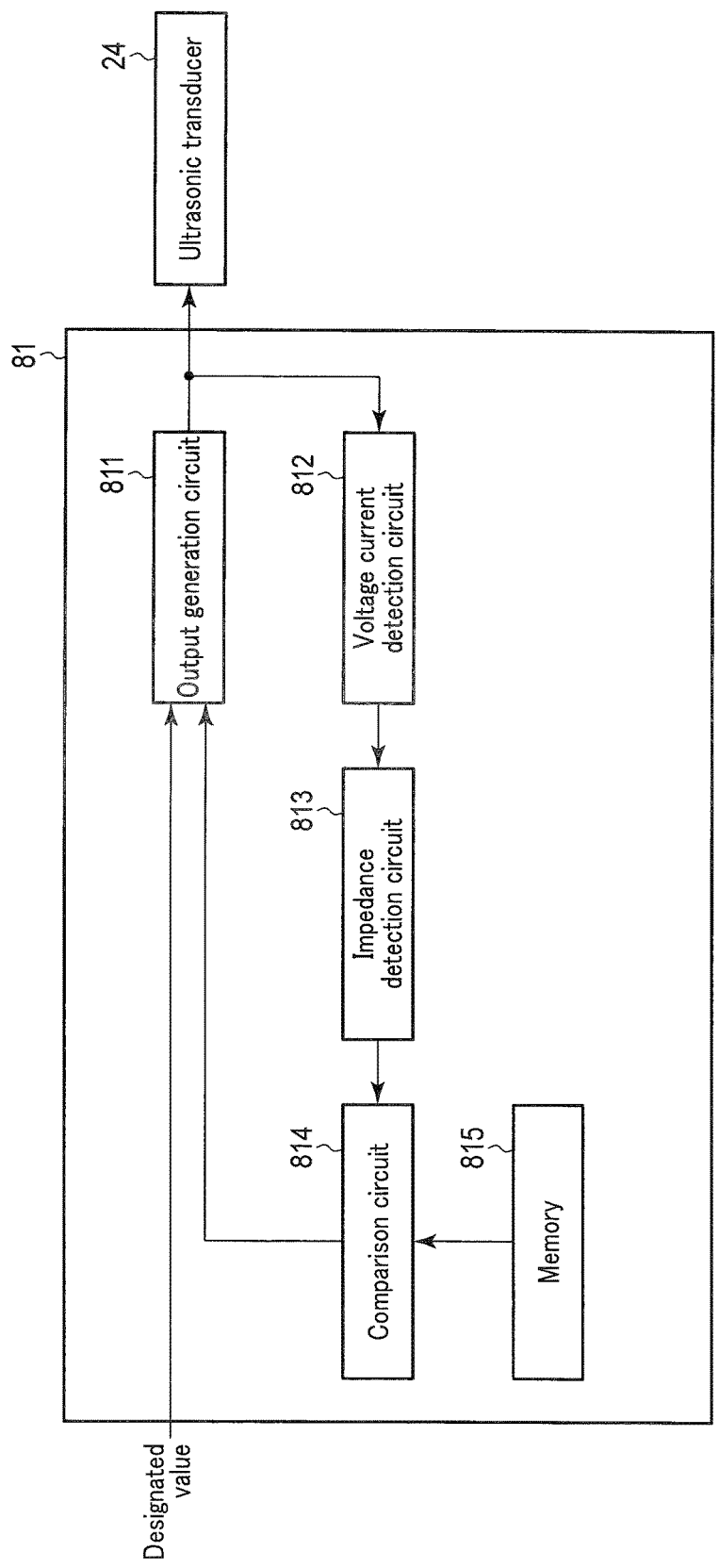
FIG. 7 is a block diagram showing a configuration of a control circuit in a second embodiment.

FIG. 7 is a block diagram showing a configuration of a control circuit 81 in the second embodiment. The control circuit 81 includes an output generation circuit 811, a voltage current detection circuit 812, an impedance detection circuit 813, a comparison circuit 814, and a memory 815. The control circuit 81 in the second embodiment is configured to return the output of the comparison circuit 814 to the output generation circuit 811.

Like the output generation circuit 811 in the first embodiment, the output generation circuit 811 in the second embodiment controls drive power so that ultrasonic vibrations of different amplitudes are generated in the cortical bone/cancellous bone cutting mode and the cartilage cutting mode. In the cartilage cutting mode, the output generation circuit 811 in the second embodiment performs control to increase or decrease the amplitude in accordance with the difference between the value of a current pressing force and the upper limit or lower limit of the pressing force range stored in advance. For example, the output generation circuit 811 performs control to increase or decrease the amplitude so that the current pressing value takes a value satisfying the condition that (pressing force)*(amplitude) falls within the range of 100 [N·μm]-300 [N·μm]. In the cortical bone/cancellous bone cutting mode, the output generation circuit 811 performs control to increase or decrease the amplitude in accordance with the value of the current pressing force. For example, when the pressing force is 3N or weaker, the output generation circuit 811 performs control to increase the amplitude to inhibit reduction of the cut amount. When the pressing force is 5N or stronger, the output generation circuit 811 performs control to decrease the amplitude as a safety measure for inhibiting generation of heat.

According to the present embodiment, as described above, feedback control of amplitude is performed in accordance with the difference between the value of the current pressing force and the upper limit or lower limit of the range of the pressing force stored in advance in the memory 815. Therefore, an operator can perform treatment without changing the pressing strength.

Third Embodiment

Figure 8:
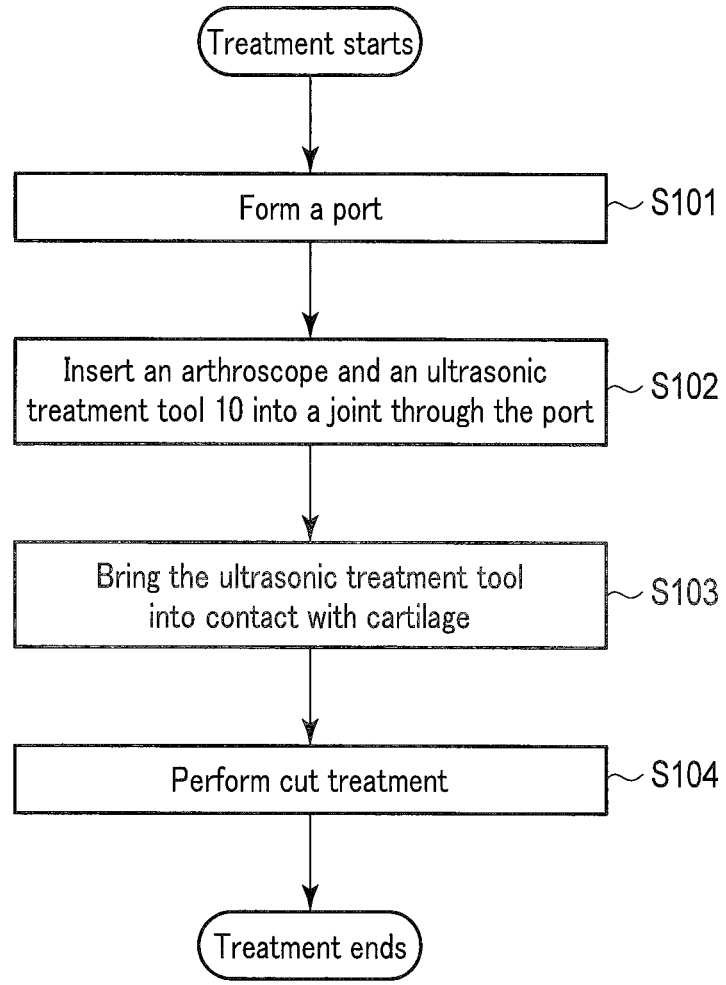
FIG. 8 is a flowchart showing a flow of treatment using the ultrasonic device.

Hereinafter, the third embodiment of the present invention will be described. The third embodiment relates to a treatment method using an ultrasonic device of the present embodiment. FIG. 8 is a flowchart showing a flow of treatment using the ultrasonic device 1. FIG. 8 shows a flow of cutting treatment of degenerating cartilage in a knee joint. The flow of FIG. 8 is applicable to treatment of not only the knee joint, but also other joints, such as a shoulder joint.

In step S101, a doctor uses a trocar to form a port to allow a treatment tool and an arthroscope to be inserted to a position of body tissue to be treated (here, degenerating cartilage in a knee joint).

In step S102, the doctor inserts an arthroscope and a treatment tool 10 of an ultrasonic device 1 through the port for the arthroscope.

In step S103, the doctor brings the cutting section 181 of the ultrasonic device 1 into contact with the degenerating cartilage to be treated while viewing an image of the inside of the knee joint displayed on a monitor via the arthroscope.

In step S104, the doctor operates, for example, the input section 22 to set the ultrasonic device 1 in a cartilage dissolution mode, and performs cutting while pressing the treatment tool against the degenerating cartilage and confirming how much the treatment tool is pressed. When the doctor's pressing is strong, a message indicating strong pressing, such as "pressing is too strong" is displayed on the monitor 82, for example, and the doctor can continue treatment with weaker pressing while viewing the monitor 82 without stopping the manipulation. When pressing becomes appropriate as a result, a message such as "pressing is appropriate" is displayed on the monitor 82, and the doctor performs treatment while keeping the current pressing by viewing the monitor 82. When the doctor's pressing is weak, a message indicating weak pressing, such as "pressing is too weak" is displayed on the monitor 82, for example, and the doctor can continue treatment with stronger pressing while viewing the monitor 82 without stopping the manipulation. When pressing becomes appropriate as a result, a message such as "pressing is appropriate" is displayed on the monitor 82, and the doctor performs treatment while keeping the current pressing by viewing the monitor 82.

According to the present embodiment, as described above, a doctor can intuitively know whether the cut amount is small due to too weak pressing or treatment is proceeding with heat intrusion to surrounding tissue due to too strong pressing by a voice or a display of a monitor, and thus can perform efficient and safe surgery with little heat intrusion without stopping the manipulation.

When the system described in the second embodiment is used, the doctor can proceed with surgery without regard to the pressing force.

The present invention has been described based on embodiments: however, the present invention is not limited to the above-described embodiments. Needless to say, various modifications or applications can be made without departing from the spirit and scope of the present invention. For example, in each of the above-described embodiments, the pressing force is detected based on the impedance of the ultrasonic transducer. However, the pressing force need not be detected based on the impedance of the ultrasonic transducer. For example, the pressing force may be detected by a sensor that directly detects a force, such as a distortion gage. Alternatively, the pressing force may be detected based on a change in the resonance frequency of the probe. The pressing force may also be detected based on temperature.

In addition, technology of identifying a state of body tissue from the impedance of an ultrasonic transducer is known. This technology may be applied to each embodiment. In this case, a range of pressing force is selected in accordance with identified body tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment method for cutting cartilage of a human body by an ultrasonic device including a cutting section that ultrasonically vibrates, the treatment method comprising:
    cutting the cartilage with a product of an amplitude of the cutting section and a pressing force for pressing the cutting section against the cartilage being 100 (N·μm) or larger.

2. The treatment method according to claim 1, wherein the ultrasonic device includes a sensor for detecting the pressing force, and
    the treatment method further comprises adjusting the amplitude to make the product of the amplitude and the pressing force 100 (N·μm) in accordance with the pressing force detected by the sensor.

3. The treatment method according to claim 1, further comprising making the product of the amplitude and the pressing force smaller than 300 (N·μm).

4. A treatment method for cutting cartilage of a human body by an ultrasonic device including a cutting section that ultrasonically vibrates, the treatment method comprising:
    cutting the cartilage with a product of an amplitude of the cutting section and a pressing force for pressing the cutting section against the cartilage being 100 (N·μm) or larger; and
    reporting to a user when the product of the amplitude and the pressing force is 100 (N·μm) or larger.

5. The treatment method according to claim 4, wherein the ultrasonic device includes a sensor for detecting the pressing force, and
    the treatment method further comprises adjusting the amplitude to make the product of the amplitude and the pressing force 100 (N·μm) in accordance with the pressing force detected by the sensor.

6. The treatment method according to claim 4, further comprising making the product of the amplitude and the pressing force smaller than 300 (N·μm).

* * * * *